(12) United States Patent
Nagatsuka et al.

(10) Patent No.: US 12,109,059 B2
(45) Date of Patent: Oct. 8, 2024

(54) DYNAMIC ANALYSIS SYSTEM, CORRECTION APPARATUS, STORAGE MEDIUM, AND DYNAMIC IMAGING APPARATUS

(71) Applicant: Konica Minolta, Inc., Tokyo (JP)

(72) Inventors: Sumiya Nagatsuka, Hino (JP); Yuki Kawana, Hino (JP)

(73) Assignee: Konica Minolta, Inc., Tokyo (JP)

( * ) Notice: Subject to any disclaimer, the term of this patent is extended or adjusted under 35 U.S.C. 154(b) by 337 days.

(21) Appl. No.: 17/318,278

(22) Filed: May 12, 2021

(65) Prior Publication Data

US 2021/0361250 A1    Nov. 25, 2021

(30) Foreign Application Priority Data

May 19, 2020 (JP) ................................ 2020-087397
May 19, 2020 (JP) ................................ 2020-087399

(51) Int. Cl.
*A61B 6/00* (2024.01)
*A61B 6/04* (2006.01)
(Continued)

(52) U.S. Cl.
CPC .............. *A61B 6/48* (2013.01); *A61B 6/0492* (2013.01); *A61B 6/08* (2013.01); *A61B 6/463* (2013.01);
(Continued)

(58) Field of Classification Search
CPC ....... A61B 6/0407; A61B 6/0492; A61B 6/08; A61B 6/462; A61B 6/48; A61B 6/486;
(Continued)

(56) References Cited

U.S. PATENT DOCUMENTS 7,826,884 B2 * 11/2010 Baumgart .............. A61B 6/481
   600/407
7,840,093 B2 * 11/2010 Fu ......................... A61N 5/1049
   382/254
(Continued)

FOREIGN PATENT DOCUMENTS

JP    H11-99142 A    4/1999
JP    2009-005827 A    1/2009
(Continued)

OTHER PUBLICATIONS

Office Action dated May 31, 2023 for the corresponding Chinese Application No. 202110539180.0, with English translation.
(Continued)

*Primary Examiner* — Dani Fox
*Assistant Examiner* — Soorena Kefayati
(74) *Attorney, Agent, or Firm* — LUCAS & MERCANTI, LLP

(57) ABSTRACT

A dynamic analysis system processes a dynamic image obtained by irradiation of a subject from a radiation irradiation apparatus and by dynamic imaging on dynamics of the subject detected by a detector. The dynamic analysis system includes a hardware processor that performs position correction of the dynamic image by eliminating an effect of displacement of the subject in a direction perpendicular to a detector plane.

11 Claims, 6 Drawing Sheets

(51) Int. Cl.
    *A61B 6/08*           (2006.01)
    *A61B 6/46*           (2024.01)
    *A61B 6/50*           (2024.01)
    *G06T 3/40*           (2024.01)
    *G06T 7/62*           (2017.01)

(52) U.S. Cl.
    CPC ............ *A61B 6/505* (2013.01); *A61B 6/5264* (2013.01); *G06T 3/40* (2013.01); *G06T 7/62* (2017.01); *A61B 6/0407* (2013.01)

(58) Field of Classification Search
    CPC ..... A61B 6/505; A61B 6/5211; A61B 6/5264; G06T 3/40; G06T 7/62
    See application file for complete search history.

(56) References Cited

U.S. PATENT DOCUMENTS

| | | | | |
|---|---|---|---|---|
| 8,594,271 | B2 * | 11/2013 | Sakaguchi | G06T 5/50 382/128 |
| 9,265,463 | B1 * | 2/2016 | Hipp | A61B 6/468 |
| 2005/0203373 | A1 * | 9/2005 | Boese | G06T 7/38 600/407 |
| 2007/0003014 | A1 * | 1/2007 | Boese | A61B 6/4476 378/95 |
| 2008/0051648 | A1 * | 2/2008 | Suri | A61B 6/5264 600/407 |
| 2009/0092305 | A1 * | 4/2009 | Ditt | G06T 7/30 382/131 |
| 2009/0180591 | A1 * | 7/2009 | Baumgart | A61B 6/463 600/407 |
| 2011/0019878 | A1 * | 1/2011 | Soubelet | G06T 7/246 382/128 |
| 2011/0069812 | A1 * | 3/2011 | Takahashi | A61B 6/4464 378/21 |
| 2011/0293164 | A1 * | 12/2011 | Sato | A61B 6/5264 382/132 |
| 2012/0059239 | A1 * | 3/2012 | Yamaguchi | A61B 6/5241 600/407 |
| 2013/0023766 | A1 * | 1/2013 | Han | A61B 6/5247 600/427 |
| 2013/0129255 | A1 * | 5/2013 | Homma | A61B 6/542 382/294 |
| 2013/0172732 | A1 * | 7/2013 | Kiraly | A61B 6/12 600/424 |
| 2014/0296657 | A1 * | 10/2014 | Izmirli | A61B 5/061 600/301 |
| 2015/0154771 | A1 * | 6/2015 | Sakaguchi | A61B 6/485 345/443 |
| 2015/0366529 | A1 * | 12/2015 | Shimizu | A61B 6/12 378/62 |
| 2016/0106389 | A1 * | 4/2016 | Lim | A61B 6/487 378/62 |
| 2016/0148398 | A1 * | 5/2016 | Takemoto | A61B 6/547 378/62 |
| 2016/0270750 | A1 * | 9/2016 | Machida | A61B 6/486 |
| 2017/0027533 | A1 * | 2/2017 | Sakaguchi | A61B 6/5264 |
| 2017/0156690 | A1 * | 6/2017 | Yi | A61B 6/5264 |
| 2017/0196529 | A1 * | 7/2017 | Lin | A61B 6/5211 |
| 2017/0243361 | A1 * | 8/2017 | Schaffert | A61B 6/5264 |
| 2018/0070894 | A1 * | 3/2018 | Osaki | A61B 6/488 |
| 2018/0082420 | A1 * | 3/2018 | Brown | G06T 7/0016 |
| 2018/0206812 | A1 * | 7/2018 | Trautwein | A61B 6/582 |
| 2018/0310905 | A1 * | 11/2018 | Yoshida | A61B 6/487 |
| 2018/0333132 | A1 * | 11/2018 | Noda | A61B 6/5264 |
| 2019/0090962 | A1 * | 3/2019 | Boettner | A61B 6/487 |
| 2019/0180481 | A1 * | 6/2019 | Fu | G06T 11/006 |
| 2019/0192101 | A1 * | 6/2019 | Manhart | A61B 6/032 |
| 2019/0223278 | A1 * | 7/2019 | Jordan | A61B 6/582 |
| 2019/0251724 | A1 * | 8/2019 | Schreckenberg | G06T 11/206 |
| 2019/0261939 | A1 * | 8/2019 | Yoshida | A61B 6/0407 |
| 2019/0320995 | A1 * | 10/2019 | Amiri | A61B 6/463 |
| 2019/0388051 | A1 * | 12/2019 | Morita | G06T 7/0012 |
| 2020/0008707 | A1 * | 1/2020 | Li | A61B 5/055 |
| 2020/0090380 | A1 * | 3/2020 | Regensburger | G06T 7/74 |
| 2020/0107884 | A1 * | 4/2020 | Razeto | A61B 6/032 |

FOREIGN PATENT DOCUMENTS

| | | |
|---|---|---|
| JP | 2009-082372 A | 4/2009 |
| JP | 2010-172416 A | 8/2010 |
| JP | 2012-005695 A | 1/2012 |
| JP | 2012-161471 A | 8/2012 |
| JP | 2012-200398 A | 10/2012 |

OTHER PUBLICATIONS

Office Action dated Sep. 26, 2023 for the corresponding Japanese Application No. 2020-087399, with English translation.

Office Action dated Oct. 10, 2023 for the corresponding Japanese Application No. 2020-087397, with English translation.

JPO, Japanese Office Action mailed May 21, 2024 for the related Japanese application No. 2020-087399, with English Machine translation, 6 pages.

\* cited by examiner

DYNAMIC ANALYSIS SYSTEM, CORRECTION APPARATUS, STORAGE MEDIUM, AND DYNAMIC IMAGING APPARATUS

CROSS-REFERENCE TO RELATED APPLICATIONS

The entire disclosure of Japanese Patent Application No. 2020-087397 filed on May 19, 2020 and No. 2020-087399 filed on May 19, 2020 is incorporated herein by reference in its entirety.

BACKGROUND

Technological Field

The present invention relates to a dynamic analysis system, a correction apparatus, a storage medium, and a dynamic imaging apparatus.

Description of Related Art

In taking a fluoroscopic image, it has been conventionally performed to correct distortion of the image and variations in the effective field of view.

For example, JP H11-99142 A discloses an X-ray diagnostic apparatus including an X-ray tube, an X-ray fluoroscopic image detector, and an image display means that displays an X-ray fluoroscopic image detected by the X-ray fluoroscopic image detector. In the X-ray diagnostic apparatus, the image magnification of the X-ray fluoroscopic image projected on the X-ray sensor of the X-ray fluoroscopic image detector is obtained, and points on the X-ray fluoroscopic image displayed on the screen of the image display means are appropriately designated. Based on the obtained image magnification and position information of the two designated points, actual dimensions on the subject corresponding to the distance between the two designated points on the transmission X-ray image are calculated and the calculated dimensions are displayed.

In taking a long image, it has been conventionally performed to correct magnification of the subject at an overlapping part(s) of radiographic images to be combined.

For example, JP 2010-172416 A discloses an X-ray imaging apparatus including an X-ray tube, an X-ray detector, an X-ray tube driving means that rotates and moves the X-ray tube in order to change the X-ray irradiation angle, a control means that drives and controls the X-ray tube driving means, an image generation means that generates an image of a subject based on a transmission X-ray signal, and an image correction means that reduces or enlarges the image that is taken at a certain rotation angle of the X-ray tube at a magnification corresponding to the rotation angle.

SUMMARY

In dynamic imaging, depending on a movement of the subject to be imaged, the diagnosis target part may be inevitably displaced in a direction perpendicular to a detector plane of a detector (radiation detector) (hereinafter, an orthogonal direction) (for example, in taking an image of a pelvis during standing and sitting movements, or a knee during upward and downward movements).

Also, even when taking an image of movements that does not usually cause displacement of the diagnosis target part in the orthogonal direction, the diagnosis target part may be unavoidably displaced in the orthogonal direction due to wobbling of the subject (especially the elderly), momentum as a result of the movement, and the like.

When the diagnosis target part is displaced in the orthogonal direction as described above, the diagnosis target part in the radiographic image appears to have different sizes.

When the size of the diagnosis target part is different in respective frames, it becomes difficult for the diagnostician (doctor) to accurately diagnose the diagnosis target part. As a result, the diagnostician may make a mistake in the diagnosis and in the subsequent treatment (for example, in selection of artificial bone).

Furthermore, depending on movement to be imaged (for example, standing movement with a load), it may be difficult for the subject (particularly the elderly) to move without wobbling.

In such cases, a photographer (technician) needs to pay attention to wobbling of the subject while taking an image. Furthermore, when the subject has wobbled, it is necessary to take an image again.

On the other hand, it is hard for the subject to keep moving without wobbling. Furthermore, if it becomes necessary to retake the images due to wobbling, the subject will be exposed to a larger amount of radiation.

That is, it has been a heavy burden for both the photographer and the subject to take an image of a movement that tends to induce wobbling.

Objects of the present invention include reducing the burden on both the photographer and the subject while a dynamic image is taken, and enabling a diagnostician to make an accurate diagnosis based on the dynamic image.

To achieve at least one of the above-mentioned objects, according to an aspect of the present invention, there is provided a dynamic analysis system that processes a dynamic image obtained by irradiation of a subject from a radiation irradiation apparatus and by dynamic imaging on dynamics of the subject detected by a detector, including:

a hardware processor that performs position correction of the dynamic image by eliminating an effect of displacement of the subject in a direction perpendicular to a detector plane.

To achieve at least one of the above-mentioned objects, according to another aspect of the present invention, there is provided a correction apparatus that processes a dynamic image obtained by irradiation of a subject from a radiation irradiation apparatus and by dynamic imaging on dynamics of the subject detected by a detector, including:

a hardware processor that performs position correction of the dynamic image by eliminating an effect of displacement of the subject in a direction perpendicular to a detector plane.

To achieve at least one of the above-mentioned objects, according to another aspect of the present invention, there is provided a non-transitory computer-readable storage medium storing a program causing a hardware processor of a correction apparatus that processes a dynamic image obtained by irradiation of a subject from a radiation irradiation apparatus and by dynamic imaging on dynamics of the subject detected by a detector, to perform:

position correction of the dynamic image by eliminating an effect of displacement of the subject in a direction perpendicular to a detector plane.

To achieve at least one of the above-mentioned objects, according to another aspect of the present invention, there is provided a dynamic imaging apparatus that obtains a dynamic image by irradiation of a subject from a radiation irradiation apparatus and by dynamic imaging on dynamics of the subject detected by a detector, including:

a jig that restricts movement of the subject in a direction perpendicular to a detector plane.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention, wherein.

DETAILED DESCRIPTION OF THE EMBODIMENTS

Hereinafter, one or more embodiments of the present invention will be described with reference to the drawings. However, the scope of the invention is not limited to the disclosed embodiments.

First Embodiment

First, the first embodiment of the present invention will be described.

[Dynamic Analysis System]

Figure 1:
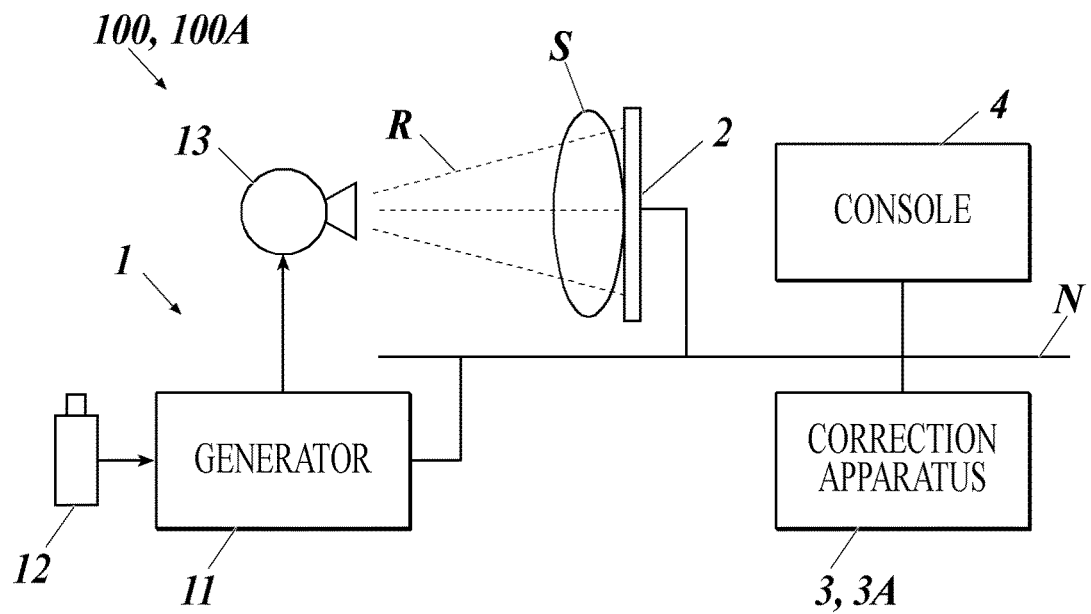
FIG. 1 is a block diagram of a dynamic analysis system according to an embodiment of the present invention.
Figure 2:
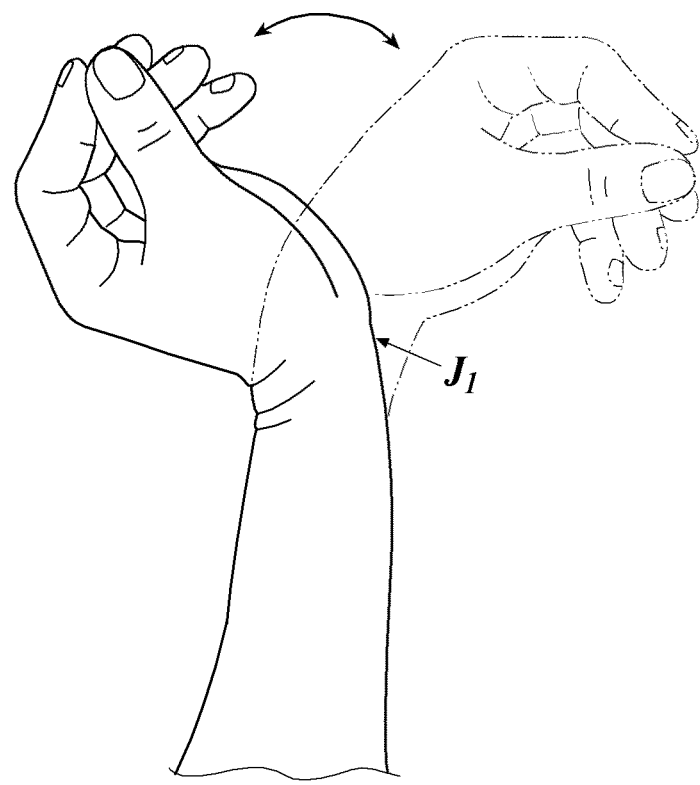
FIG. 2 is a diagram showing an example of a movement of a subject.

First, a schematic configuration of the dynamic analysis system (hereinafter, system 100) according to the present embodiment will be described. FIG. 1 is a block diagram showing the system 100, and FIGS. 2 and 3 are diagrams showing an example of the operation of the subject S.

Among the reference numerals separated by punctuation marks in FIG. 1, the reference numerals after the punctuation marks will be described in the second embodiment below.

As shown in FIG. 1, the system 100 includes a radiation irradiation apparatus 1, a detector 2 (a radiation detector), and a correction apparatus 3.

The system 100 according to the present embodiment further includes a console 4.

The devices 1 to 4 can communicate with each other via, for example, a communication network N (LAN (Local Area Network), WAN (Wide Area Network), the Internet, and the like.)

The system 100 may be capable of communicating with a Hospital Information System (HIS), a Radiology Information System (RIS), a Picture Archiving and Communication System (PACS), and the like (not shown).

(Radiation Irradiation Apparatus)

The radiation irradiation apparatus 1 includes a generator 11, an irradiation instruction switch 12, and a radiation source 13.

The radiation irradiation apparatus 1 may be installed in an imaging room, or may be configured to be movable together with the console 4 and the like as a mobile vehicle.

The generator 11 applies a voltage corresponding to a preset imaging condition(s) to the radiation source 13 (tube) in response to the operation of the irradiation instruction switch 12. The preset imaging condition(s) includes, for example, a condition related to the subject S, such as the part to be imaged, imaging direction, and physique, or a condition related to radiation R irradiation such as tube voltage, tube current, irradiation time, current time product (mAs value), and the like.

When a voltage is applied from the generator 11, the radiation source 13 generates radiation R (for example, X-rays) of a dose corresponding to the applied voltage.

The radiation source 13 can move in an X-axis direction, a Y-axis direction perpendicular to the X-axis, and a Z-axis direction perpendicular to the X-axis and the Y-axis. The radiation source 13 can further rotate around a rotation axis that is parallel to the Y-axis and a rotation axis that is parallel to the Z-axis to change the direction of the radiation irradiation port.

The radiation irradiation apparatus 1 configured as described above can generate radiation R according to the imaging mode (for taking still image or dynamic image).

The radiation irradiation apparatus 1 can irradiate any part (for example, bone, joint, etc.) of the subject S in any posture (standing, lying, sitting, etc.) with radiation R at any angle to the part (i.e., to a plane parallel to or a line vertical to the part).

(Detector)

Although not shown in the drawings, the detector 2 includes the followings: a sensor substrate that has a detector plane 2a (imaging surface, radiation incident surface, and the like) in which pixels having radiation detection elements and switch elements are arranged in a two-dimensionally (in a matrix shape); a scanning circuit that switches on/off of the respective switch elements; a readout circuit that reads out the amount of charge released from the respective pixels as signal values; a control unit that generates a radiographic image based on the signal values read by the readout circuit; a communication unit that transmits the generated radiation image data and various signals to the outside and receives various kinds of information and various signals; and the like. In response to receiving radiation, the radiation detection element generates electric charge according to the dose, and the switch elements stores and releases electric charge.

The detector 2 generates a radiation image depending on the dose of the emitted radiation R by accumulating and releasing electric charges and reading the signal values in synchronization with the timing of the radiation R from the radiation irradiation apparatus 1.

In particular, when an image of a movement of the subject S is taken, a dynamic image including a plurality of frames is generated by charge accumulation, charge release, and signal value reading that are repeated multiple times in a short period of time (for example, 15 times per second).

That is, the detector 2 functions as a moving image generation means.

As shown in FIG. 1, the detector plane 2a can be arranged at a place that the radiation R enters after being emitted in a direction so as to pass through the subject S.

The detector 2 may be arranged alone, or may be supported by a table or the like (not shown).

(Correction Apparatus)

The correction apparatus 3 functions as a correction means, and includes a personal computer (PC), a dedicated device, and the like.

The details of this correction apparatus 3 will be described later.

(Console)

The console 4 includes a PC, a dedicated device, and the like.

The console 4 can set various imaging conditions (tube voltage, tube current, irradiation time (mAs value), a part to be imaged, an imaging direction, and the like) in the imaging apparatus or the like based on order information obtained from other systems (HIS, RIS, and the like) or user operations.

In the system 100 illustrated in FIG. 1, the console 4 is provided separately from the correction apparatus 3, but the console 4 may be integrated with the correction apparatus 3.

(Outline of Operation of Dynamic Analysis System)

In the system 100 configured as described above, the radiation source 13 of the radiation irradiation apparatus 1 is arranged so as to face the detector 2 with a gap between them and irradiates the subject S arranged in the gap with the radiation R. This makes it possible to take a radiographic image of the subject S (to generate a radiographic image corresponding to the radiation R through the subject S).

When taking an image of a subject in a still state, emission of the radiation R and generation of a radiation image are each performed only once in response to one imaging operation (pressing of the irradiation instruction switch 12). When taking an image of a moving subject, emission of pulsed radiation R and generation of a frame are each performed repeatedly (multiple times) in a short time in response to one imaging operation.

(Subject to be Imaged by Dynamic Analysis System)

The correction apparatus 3 corrects the dynamic image generated by the detector 2 so as to eliminate the effect of displacement of the subject S in the direction perpendicular to the detector plane 2a.

Therefore, the system 100 according to the present embodiment is suitable for taking an image of the subject S in movement that tends to cause displacement in a perpendicular direction to the detector plane 2a.

The subject S in such a case is, for example, a mark attached to a specific part or a vicinity thereof.

The specific part is, for example, a bone, joint, or spine.

The movement of the subject S that tends to cause displacement in a perpendicular direction to the detector plane 2a is, for example, extension and flexion movement of a wrist joint $J_1$ (movement in throwing darts) as shown in FIG. 2.

In this movement, the hand swings as a result of the extension and flexion of the wrist joint $J_1$. With the momentum of the swinging hand, the forearm is displaced depending on the direction of the swing. As a result, the wrist joint $J_1$ is also displaced together with the forearm. When the hand swings in the direction perpendicular to the detector plane 2a, the wrist joint $J_1$ is also displaced in the direction perpendicular to the detector plane 2a.

Figure 3A:
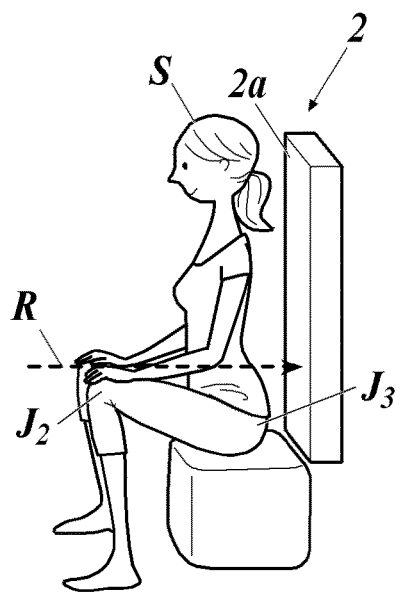
FIG. 3A to FIG. 3C are diagrams showing another example of a movement of the subject.
Figure 3B:
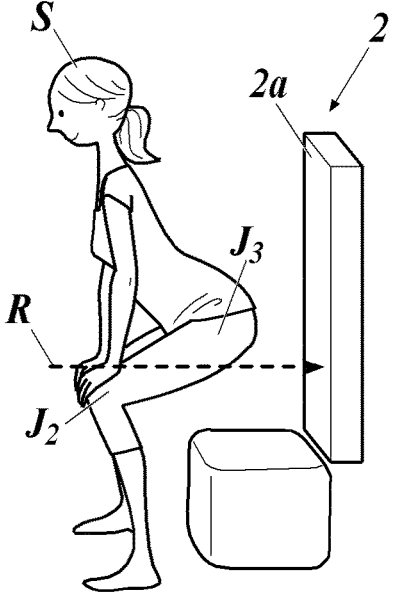
Figure 3C:
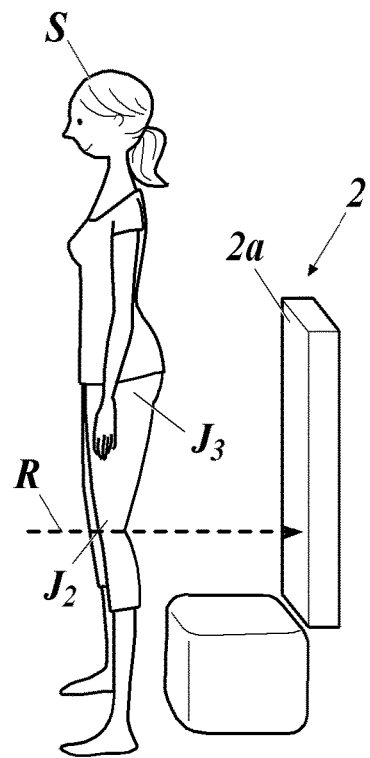

The movement of the subject S that can cause displacement of the subject S in the direction perpendicular to the detector plane 2a includes, as shown in FIG. 3A to FIG. 3C, for example, extension and flexion of a knee joint $J_2$ and a hip joint $J_3$ (movement in standing from a chair or sitting on a chair).

In this movement, a thigh and torso move up and down as a result of the extension and flexion of the knee joint $J_2$ and the hip joint $J_3$. At that time, the hip joint $J_3$ is displaced between a position on the lateral side of the knee (position shown in FIG. 3A) and a position above the knee (position shown in FIG. 3C). When the detector plane 2a is in front of or behind the subject S, the hip joint $J_3$ is displaced in the direction perpendicular to the detector plane 2a.

In the middle of standing or sitting (while his or her hip is above the chair), the subject S tilts the lower legs as shown in FIG. 3B for balance, which may cause displacement of the knee joints $J_2$ in a direction depending on the tilt of the lower legs.

Also in the middle of standing or sitting, the subject S may lose his balance and wobble, which results in displacement of the knee joints $J_2$.

When the direction in which the lower legs are tilted or the subject S wobbles is perpendicular to the detector plane 2a, the knee joints $J_2$ are also displaced in a direction perpendicular to the detector plane 2a.

[Correction Apparatus]

Next, configurations of the correction apparatus 3 in the system 100 will be described.

Figure 4:
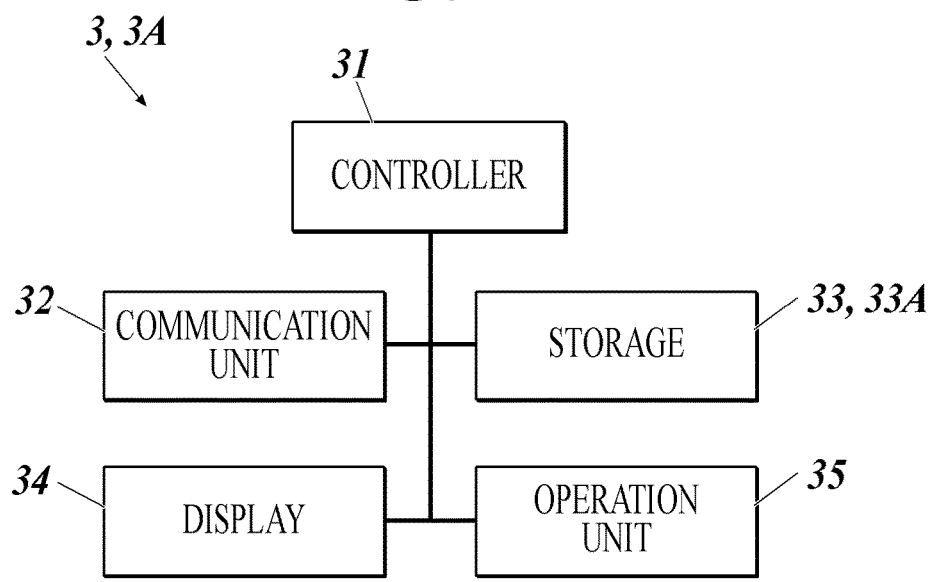
FIG. 4 is a block diagram of a correction apparatus of the dynamic analysis system of FIG. 1.
Figure 5:
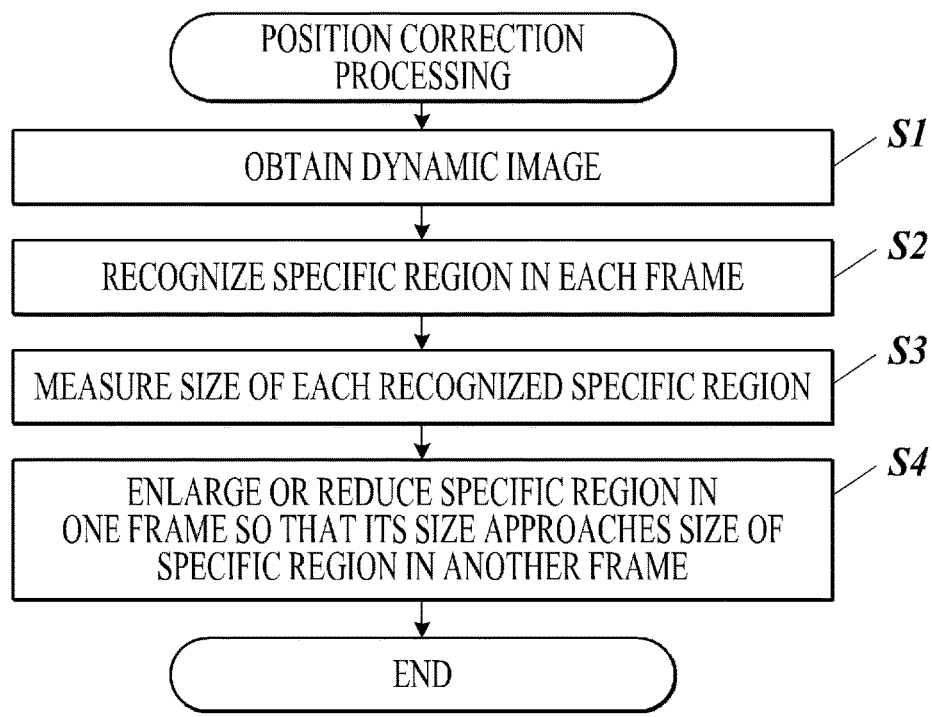
FIG. 5 is a flowchart showing a flow of the position correction processing executed by the correction apparatus of the dynamic analysis system according to the first embodiment.

FIG. 4 is a block diagram of the correction apparatus 3. FIG. 5 is a flowchart showing the flow of the position correction processing executed by the correction apparatus 3.

Among the reference numerals separated by punctuation marks in FIG. 4, the reference numerals after the punctuation marks will be described in the second embodiment below.

(Configuration of Correction Apparatus)

As shown in FIG. 4, the correction apparatus 3 includes a controller 31 (hardware processor), a communication unit 32, and a storage 33.

The correction apparatus 3 according to the present embodiment further includes a display 34 and an operation unit 35.

The units 31 to 35 are electrically connected to each other by a bus or the like.

The controller 31 includes a CPU (Central Processing Unit), a RAM (Random Access Memory), and the like.

The CPU of the controller 31 reads various programs stored in the storage 33, loads them in the RAM, executes various processes according to the loaded programs, and centrally controls the operation of each of the units of the correction apparatus 3.

The communication unit 32 includes a communication module and the like.

The communication unit 32 sends and receives various signals and data to and from the device(s) (for example, the detector 2 and the console 4) connected via the communication network N.

The correction apparatus 3 may include a reading unit capable of reading the contents stored in a storage medium instead of the communication unit 32, and take in various kinds of data using the storage medium.

The storage 33 includes a non-volatile semiconductor memory, a hard disk, or the like.

The storage 33 stores various programs executed by the controller 31 (including position correction processing described later), parameters necessary for executing the programs, and the like.

The storage 33 may be able to store the radiographic image(s).

The display 34 includes a monitor that displays an image, such as an LCD (Liquid Crystal Display) or a CRT (Cathode Ray Tube).

The display 34 displays various images and the like based on the control signal(s) that is input from the controller 31.

The operation unit 35 according to the present embodiment includes a keyboard having cursor keys, numeric keys, and various function keys, a pointing device such as a mouse, a touch panel laminated on the surface of the display 34, and the like.

The operation unit 35 outputs a control signal corresponding to the operation by the user to the controller 31.

The console 4 may also serve as at least one of the display 34 and the operation unit 35.

(Operation of Correction Apparatus)

The controller 31 of the correction apparatus 3 configured as described above has the following functions.

Position Correction Function

For example, when a predetermined condition is satisfied, the controller 31 performs position correction processing as shown in FIG. 5.

The "predetermined condition" includes, for example, that the correction apparatus 3 is turned on, the correction apparatus 3 is connected to the communication network N, the operation unit 35 has received a predetermined start operation, the communication unit 32 receives a predetermined control signal from other device(s), and the like.

In this position correction processing, the controller 31 first executes an obtaining process (step S1).

In this obtaining process, the controller 31 obtains, from another device (detector 2, console 4, or the like), a dynamic image in which a movement of the subject S is captured.

The controller 31 according to the present embodiment obtains the dynamic image by receiving data via the communication unit 32.

Alternatively, the controller 31 may obtain the dynamic image by reading data stored in a storage medium.

Alternatively, the controller 31 may start the position correction processing when the dynamic image is obtained. In that case, it is not necessary to execute the obtaining process in this position correction processing.

The controller 31 functions as an obtaining means by executing the obtaining process described above.

After obtaining the dynamic image, the controller 31 executes a recognition process (step S2).

In this recognition process, the controller 31 recognizes a specific region in which the subject S is captured in each of the frames constituting the dynamic image.

The specific region can be recognized by a method using any conventionally known technique.

The controller 31 functions as a recognition means by executing the recognition process described above.

After recognizing the specific region in each of the frames, the controller 31 executes a measurement process (step S3).

In this measurement process, the controller 31 measures the size of recognized specific region in each of the frames.

The size can be measured by a method using any conventionally known technique.

The controller 31 functions as a measurement means by executing the measurement process described above.

After measuring the size of the specific region in each of the frames, the controller 31 executes a size change process (step S4) and finishes the position correction processing.

In this size change process, the controller 31 enlarges or reduces an image captured in one of the frames based on the measured size of the specific region, such that the size of the specific region in the one frame gets closer to the size of the specific region in another frame as a reference frame.

In the size change process according to the present embodiment, the image is enlarged or reduced such that the size of the specific region captured in all the frames are uniform (within a predetermined range).

When the size of the specific region is substantially the same in all the frames, the movement of the subject S is corrected so that the effects of displacement in the direction perpendicular to the detector plane 2a is eliminated.

The controller 31 functions as a size change means by executing the size change process described above.

Saving Function

The controller 31 according to the present embodiment further has a function of saving the dynamic image corrected in the above position correction processing.

Specifically, the controller 31 saves (stores in the storage 33) at least a part of the frames of the dynamic image that has been corrected in the above position correction processing.

The controller 31 according to this embodiment can store all the frames.

The controller 31 may be configured to save the dynamic image in the above position correction processing.

The controller 31 may cause the dynamic image to be sent to and stored in another device having a saving means (console 4, a server (not shown), or the like), instead of storing in the storage 33 as described above.

The controller 31 and storage 33 serves as a saving means by having such a saving function.

Display Function

The controller 31 according to the present embodiment has a function of displaying the dynamic image that has been corrected in the position correction processing on the display 34.

The controller 31 and the display 34 serve as a display means by having such a display function.

Effects

In the system 100 according to the present embodiment described above, the correction apparatus 3 corrects the dynamic image so as to eliminate the effects of displacement of the subject S in the direction perpendicular to the detector plane 2a by making the size of the specific region where the subject S is captured in each of the frames substantially the same.

Therefore, according to the system 100, it is possible to reduce the burden on both the photographer and the subject while a dynamic image is taken, and to enable a diagnostician to make an accurate diagnosis based on the dynamic image.

Second Embodiment

Next, the second embodiment of the present invention will be described.

In the followings, the same components as those in the first embodiment will be designated by the same reference numerals, and the description thereof will be omitted.

[Dynamic Analysis System]

First, the differences between the dynamic analysis system according to the present embodiment (hereinafter, a system 100A) and the system 100 according to the above first embodiment will be described.

The system 100A includes an optical camera.

Furthermore, the system 100A is different from the first embodiment in that a content of process executed by a correction apparatus 3A of the system 100A (a program stored in a storage 33A) is different from that by the correction apparatus 3 according to the first embodiment.

The correction apparatus 3A also corrects the dynamic image so as to eliminate the effects of displacement of the subject S in the direction perpendicular to the detector plane as the correction apparatus 3 according to the above first embodiment. However, the specific method of the correction is different from the correction apparatus 3 according to the first embodiment.

[Correction Apparatus]

Next, the difference between the control executed by the correction apparatus 3A and the control executed by the correction apparatus 3 according to the first embodiment will be described.

Figure 6:
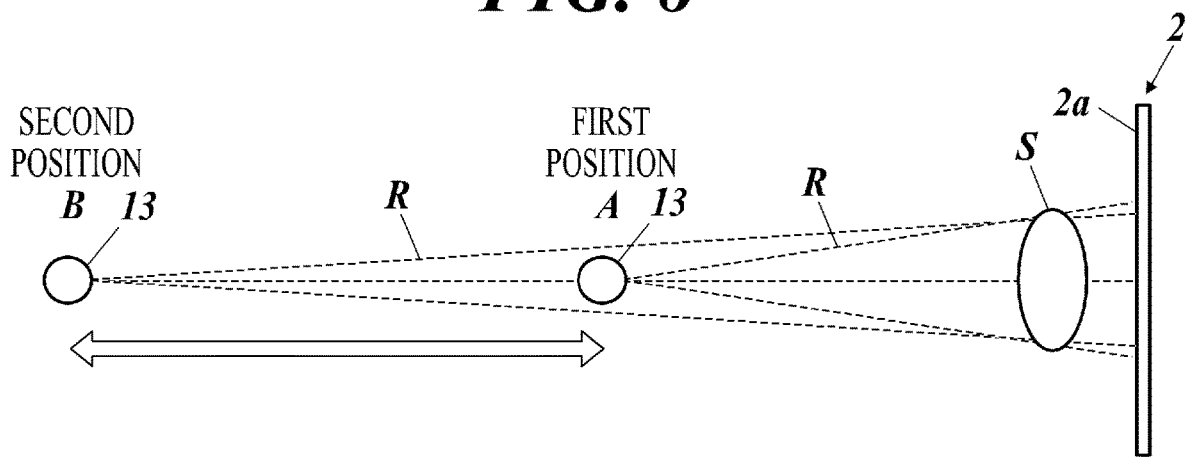
FIG. 6 is a diagram showing operation of a dynamic analysis system according to the second embodiment during imaging.
Figure 7:
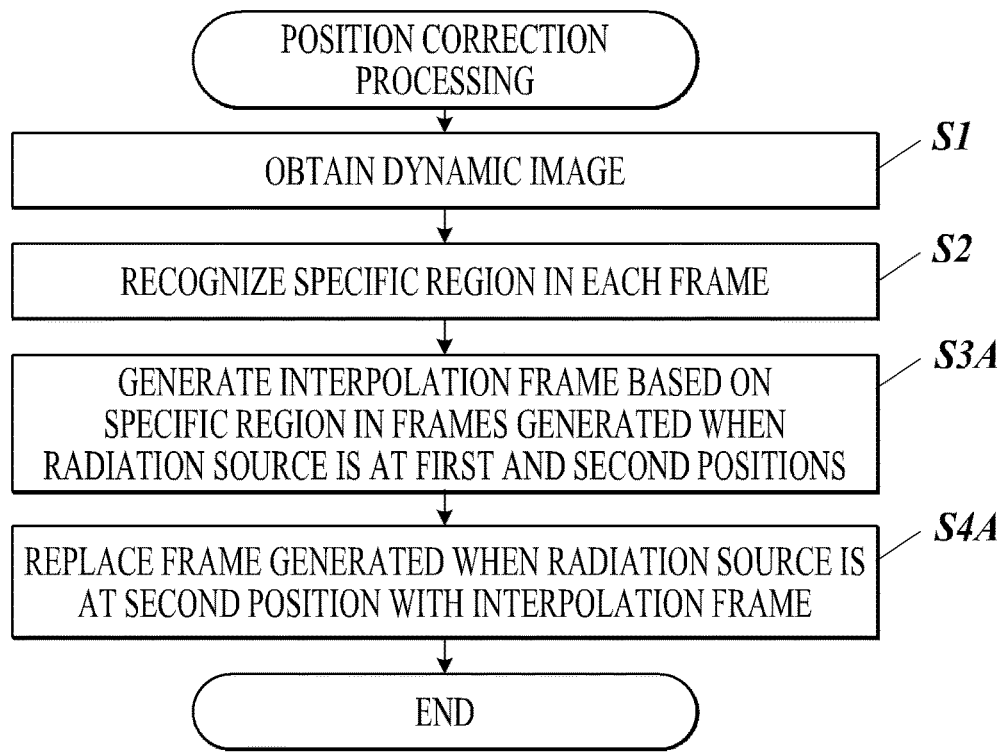
FIG. 7 is a flowchart showing a flow of the position correction processing executed by the correction apparatus of the dynamic analysis system according to the second embodiment.
Figure 8:
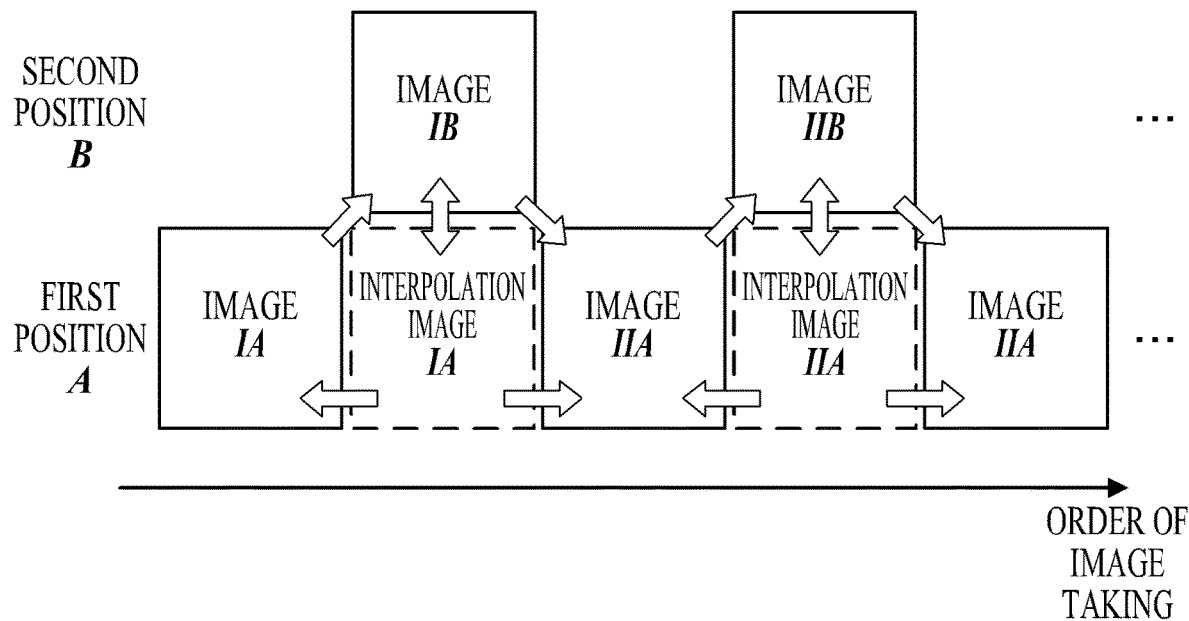
FIG. 8 is a conceptual diagram of an interpolation process executed in the position correction processing of FIG. 7.

FIG. 6 is a diagram showing an operation when the dynamic analysis system according to the second embodiment takes an image. FIG. 7 is a flowchart showing a flow of position correction processing executed by the correction apparatus of the dynamic analysis system according to the second embodiment. FIG. 8 is a conceptual diagram of an interpolation process executed in the position correction processing.

Position Control Function

The controller 31 of the correction apparatus 3A executes the position control process when, for example, the interlock of the radiation irradiation apparatus 1 is released, the irradiation instruction switch 12 is operated, or the like.

In the position control process while an image of the subject S is taken, the controller 31 moves the radiation source 13 to a first position A and a second position B as shown in FIG. 6, for example. The first position A is separated from the detector plane 2a by a first distance in the direction perpendicular to the detector plane 2a. The second position B is separated from the detector plane 2a by a second distance in the direction perpendicular to the detector plane 2a. The second distance is longer than the first distance.

In the control process according to the present embodiment, the controller 31 monitors whether or not the subject S is displaced in the direction perpendicular to the detector plane 2a based on the optical image taken by the optical camera. Then, when detecting the displacement of the subject S in the perpendicular direction to the detector plane 2a, the controller 31 moves the radiation source 13 to the second position B.

The controller 31 functions as a monitoring means and a movement control means by executing the position control process described above. That is, when the subject S is displaced in the direction perpendicular to the detector plane 2a while an image is taken, the controller 31 generates a dynamic image including a frame(s) generated when the radiation source 13 is at the first position A and a frame(s) generated when the radiation source 13 is at the second position B.

Position Correction Function

When a predetermined condition is satisfied, the controller 31 executes position correction processing as shown in FIG. 7, for example.

The "predetermined condition" is the same as the one described in the first embodiment.

In the position correction processing, the controller 31 first executes the obtaining process (step S1), and then executes the recognition process (step S2).

The contents of the obtaining process and the recognition process, and their modifications are the same as those in the first embodiment.

After recognizing the specific region in the frames, the controller 31 executes the interpolation process (step S3A).

In this interpolation process, the controller 31 generates, as shown in FIG. 8, an interpolation frame(s) based on the specific region in a frame generated when the radiation source is in the first position A and the specific region in a frame generated when the radiation source is in the second position B.

The interpolation frame is a frame including the specific region that is assumed to be captured when the radiation source 13 is at an infinite distance from the detector plane 2a.

Specifically, the outline of the specific region is plotted for each of the frames, and the size of the outline of the specific region when the Source-to-Image Distance (SID) is set to $\infty$ (infinity) is determined.

When the radiation source 13 is at an infinite distance from the detector plane 2a, all the radiation is perpendicular to the detector plane 2a. Therefore, even when the subject S moves in the direction perpendicular to the detector plane 2a, the change in the size of the specific region in each frame becomes small. In other words, the size of the specific region when the SID is $\infty$ can be regarded as the size of the specific region when there is no displacement in a perpendicular direction to the detector plane 2a.

Then, the magnification of the specific region in the frame calculated when the radiation source is at the second position B with respect to the specific region when the SID is $\infty$ is calculated.

Then, an interpolation frame is generated by reducing the frame generated when the radiation source is at the second position B in size by a reciprocal of the calculated magnification.

The controller 31 functions as an interpolation means by executing the interpolation process described above.

After generating the interpolation frame, the controller 31 executes a replacing process (Step S4A).

In this replacing process, the controller 31 replaces the frame generated when the radiation source 13 is at the second position B in the dynamic image with the interpolation frame.

When the frame generated when the radiation source 13 is at the second position B is replaced by the interpolation frame, the movement of the subject S is corrected such that the effects of displacement in the direction perpendicular to the detector plane 2a is eliminated.

The controller 31 functions as a replacement means by executing the replacing process described above.

Effects

In the system 100A according to the present embodiment described above, the correction apparatus 3A corrects the dynamic image so as to eliminate the effects of displacement of the subject S in the direction perpendicular to the detector plane 2a by replacing the frame generated when the radiation source 13 is at the second position B with the interpolation frame.

Therefore, according to the system 100A, as well as the system 100 in the first embodiment, it is possible to reduce the burden on both the photographer and the subject while a dynamic image is taken, and to enable a diagnostician to make an accurate diagnosis based on the dynamic image.

Third Embodiment

Next, the third embodiment of the present invention will be described.
(Jig)

Figure 9A:
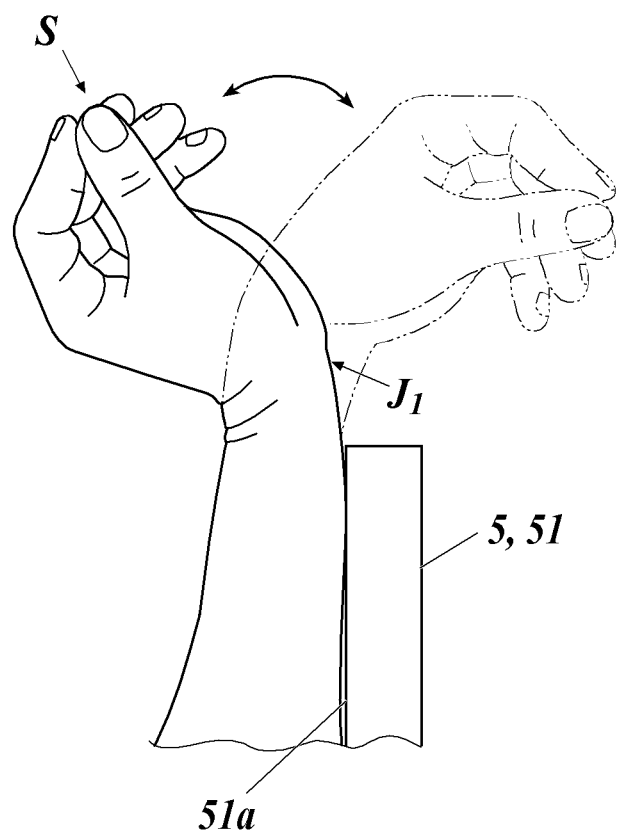
FIG. 9A and FIG. 9B are diagrams each showing an example of a method of taking an image of a subject.
Figure 9B:
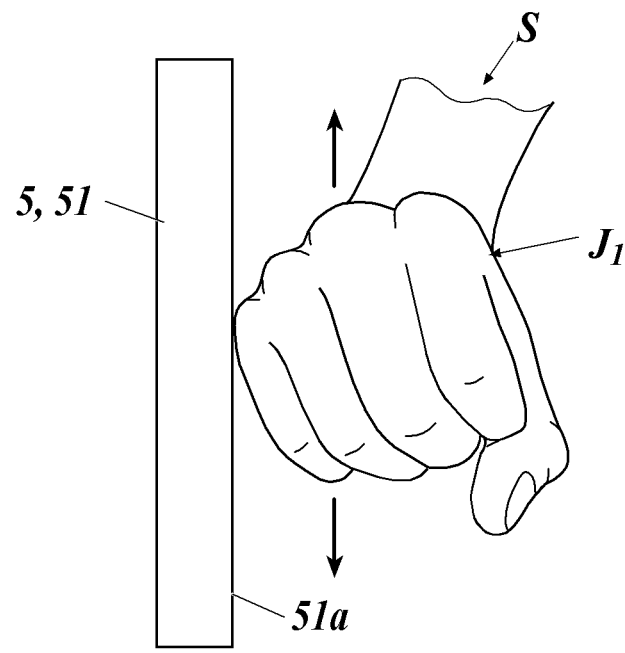

The dynamic imaging apparatus includes a jig 5 (FIG. 9A and FIG. 9B).

The jig 5 can restrict the movement of the subject S in the direction perpendicular to the detector plane.

The jig 5 according to this embodiment has a support and a restriction section 51 as shown in FIG. 9A and FIG. 9B, for example.

The support fixes the restriction section 51.

The support according to this embodiment is a rod-shaped member that extends from the floor, wall, ceiling, radiation irradiation apparatus, table for imaging, and the like in an imaging place to where the subject S will be located during imaging.

The restriction section 51 is fixed by the support.

The restriction section 51 according to this embodiment is attached to the tip of the support.

The restriction section 51 is made of a material that does not interfere with transmission of radiation.

The restriction surface 51a according to this embodiment is provided in parallel with the detector plane and at a position where the subject S comes into contact during imaging.

The restriction section 51 may be located on the detector side of the subject S, and the restriction surface 51a faces the radiation irradiation apparatus. Alternatively, the restriction section 51 may be located on the radiation irradiation apparatus side of the subject S, and the restriction surface 51a faces the detector.

The support may be deformed or the restriction section 51 may be moved with respect to the support, such that the restriction section 51 is repositioned.

The restriction section 51 may have a restriction surface 51a that is wide enough to contact the entire subject S at once.
[Subject to be Imaged by Dynamic Imaging Apparatus]

As in the above first embodiment, the movement of the subject S that tends to cause movement in a perpendicular direction to the detector plane is, for example, extension and flexion movement of the wrist joint $J_1$ (movement in throwing darts) as shown in FIG. 9A and FIG. 9B.

In this movement, the hand swings as a result of the extension and flexion of the wrist joint $J_1$. With the momentum of the swinging hand, without using the jig 5, the forearm is displaced depending on the direction of the swing. As a result, the wrist joint $J_1$ is also displaced together with the forearm. When the hand swings in the direction perpendicular to the detector plane 2a, the wrist joint $J_1$ is also displaced in the direction perpendicular to the detector plane 2a.

However, as shown in FIG. 9A, for example, by placing the restriction section 51 in contact with the upper arm, it is possible to restrict the wrist joint $J_1$ from moving in the direction perpendicular to the detector plane.

When an image of the movement of the hand joint $J_1$ is taken from an angle perpendicular to a plane on which the hand moves (perpendicular to the paper surface of FIG. 9A), the restriction section 51 may be positioned such that the restriction surface 51a is in contact with the hand and parallel to the plane on which the hand moves. When the hand moves while keeping in contact with the restriction surface 51a in this way, the movement of the subject S can be imaged without movement in the direction perpendicular to the restriction plane 51a (detector plane 2a).

Fourth Embodiment

Next, the fourth embodiment of the present invention will be described.

In the followings, the same components as those in the third embodiment will be designated by the same reference numerals, and the description thereof will be omitted.
[Jig]

Figure 10:
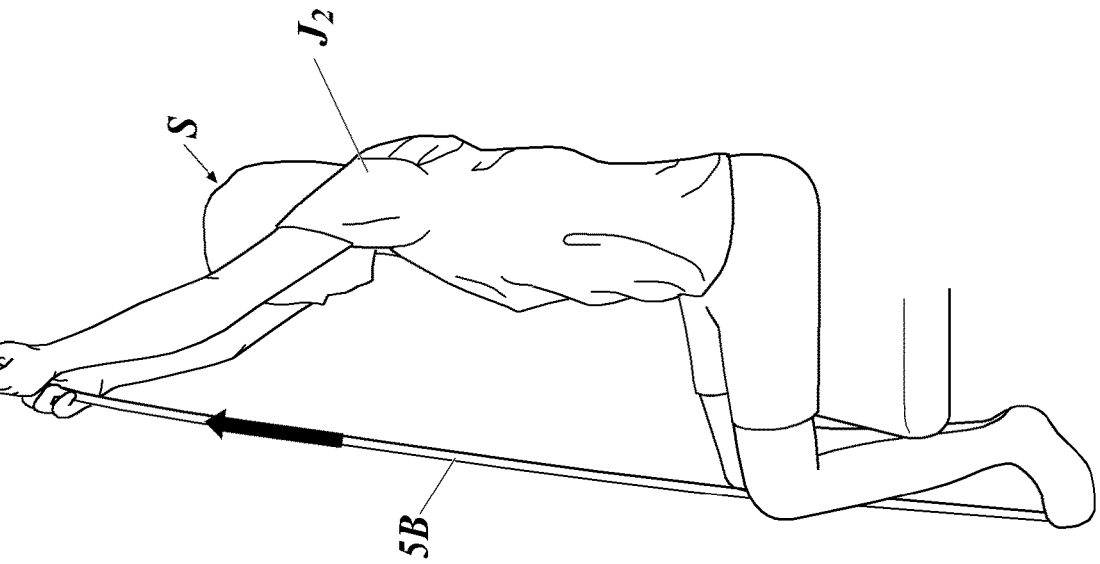
FIG. 10 is a diagram showing another example of a method of taking an image of a subject.

The dynamic imaging apparatus includes a jig 5A (FIG. 10) that is different from the jig in the third embodiment above.

The jig 5A according to the present embodiment can restrict the movement of the subject S in the direction perpendicular to the detector plane, as the jig 5 according to the above third embodiment. However, specific configurations are different between the jig 5A and the jig 5.

The jig 5A according to the present embodiment has a part that is connected to the subject S during imaging.

Specifically, the jig 5A according to this embodiment is a rubber band.

For example, when an image of the wrist joint $J_1$ is taken, one end of the rubber band is hooked on a tip of the upper arm (the part connected to the wrist joint $J_1$), the middle part thereof is stretched, and the other end thereof is fixed to the floor (for example, stepped on by the foot) or the like.

The upper arm is placed on a table or a thigh (when the subject S is in the seat).

In this way, because of the elasticity of the rubber band, the part where one end of the rubber band is hooked is fixed on the table or the thigh. As a result, it is possible to restrict the movement of the part of the subject S, on which one end of the rubber band is hooked, in the direction perpendicular to the detector plane.

The jig 5A is a simple rubber band in the above example, but the jig 5A may, for example, have a support and a cast-like restriction section that is supported by the support and that in turn supports a hand or foot of the subject S.

Fifth Embodiment

Next, the fifth embodiment of the present invention will be described.

In the followings, the same components as those in the third embodiment will be designated by the same reference numerals, and the description thereof will be omitted.
[Jig]

Figure 11:
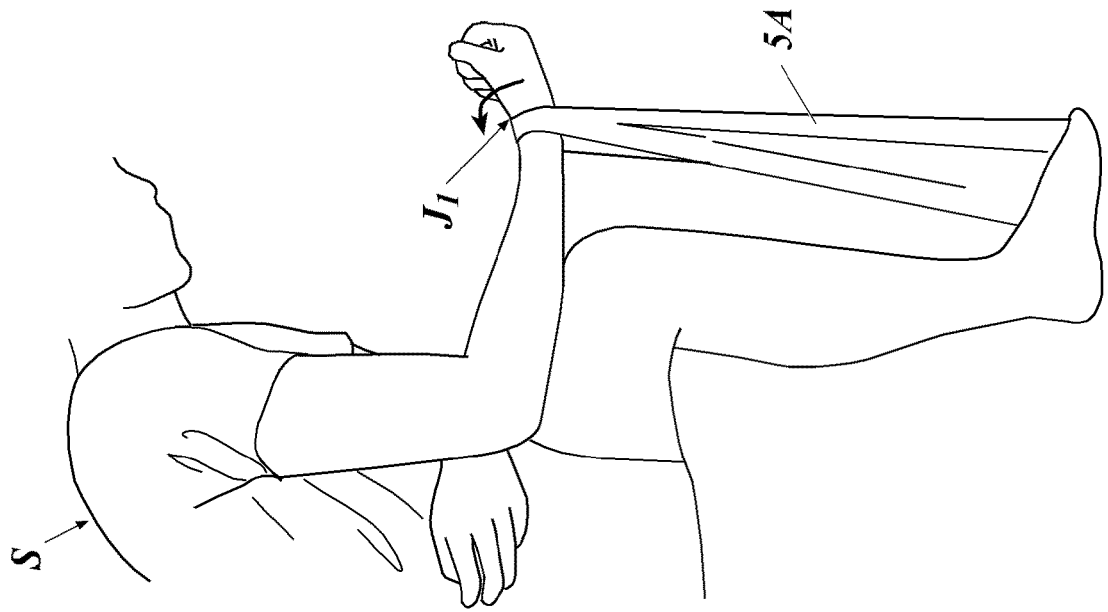
FIG. 11 is a diagram showing another example of a method of taking an image of a subject.

The dynamic imaging apparatus includes a jig 5B (FIG. 11) that is different from the third embodiment above.

The jig 5B according to the present embodiment can restrict the movement of the subject S in the direction perpendicular to the detector plane, as the jig 5 according to the above third embodiment. However, specific configurations are different between the jig 5B and the jig 5.

The jig 5B according to this embodiment has an elastic member that expands and contracts as the subject S moves in parallel with the detector plane.

Specifically, the jig 5B according to this embodiment is a rubber string. In other words, the whole jig 5B according to this embodiment is an elastic member.

For example, when a shoulder joint $J_4$ is imaged, one end of the rubber string is fixed to a hand or arm (for example, grasped by hand), and the other end thereof is fixed to the floor (for example, stepped on by the foot) or the like.

With each end of the elastic band being fixed, the subject S moves his arm up and down.

At this time, the subject S moves his arm (or a part connected to the rubber string) with a force such that the rubber string expands and contracts (vertically), taking into account of the direction in which the rubber string expands and contracts. As a result, the subject S is less likely to wobble in the direction perpendicular to the direction in which the rubber band expands and contracts (perpendicular to the detector plane).

<Others>

In the above embodiments, an image is taken for the purpose of diagnosing a specific part that moves in a specific manner (extension, flexion, and the like). However, the system 100,100A can also be used for imaging a part(s) that does not move, as long as displacement occurs in a direction perpendicular to the detector plane.

In the system 100A according to the above second embodiment, the radiation source 13 is moved in a direction perpendicular to the detector plane 2a, such that an interpolation frame is generated. Alternatively, at the first and second positions A and B, respective radiation sources 13 may be arranged for imaging with radiation from each of the positions, such that an interpolation frame similar to the one according to the second embodiment can be generated.

Furthermore, in the above embodiments, the correction apparatus 3 has the display function and the operation receiving function, however, the console 4 may have these functions instead of the correction apparatus 3.

The above description discloses an example of using a hard disk or semiconductor non-volatile memory as a computer-readable medium for the program, but the invention is not limited to this example. As other computer-readable media, it is possible to apply a portable storage medium such as CD-ROM. Carrier waves (carrier waves) are also applicable as a medium for providing the data of the program via communication lines.

Although embodiments of the present invention have been described and illustrated in detail, the disclosed embodiments are made for purposes of illustration and example only and not limitation. The scope of the present invention should be interpreted by terms of the appended claims.

What is claimed is:

1. A dynamic analysis system that processes a dynamic image obtained by irradiation of a subject from a radiation irradiation apparatus and by dynamic imaging on dynamics of the subject detected by a detector, comprising:
   a hardware processor that
      recognizes a specific region in which the subject is captured in each of the frames constituting the dynamic image,
      measures a size of the specific region that has been recognized in the each of the frames, and
      performs position correction on at least one frame of the dynamic image to ensure that a size of the specific region of the subject in the at least one frame and a size of the specific region of the subject in a reference frame of the dynamic image are within a predetermined range, thereby eliminating an effect of displacement of the subject in a direction perpendicular to a detector plane.

2. The dynamic analysis system according to claim 1, wherein
   the hardware processor
      enlarges or reduces an image captured in the at least one frame based on the size of the specific region that has been measured, thereby making a size of the specific region in the one of the frames get to within the predetermined range of the a size of the specific region in the reference frame.

3. The dynamic analysis system according to claim 1, wherein the radiation irradiation apparatus has a radiation source that moves in a direction perpendicular to the detector plane, and
   wherein the hardware processor
      moves the radiation source, while the subject is imaged, to a first position that is separated from the detector plane by a first distance in a direction perpendicular to the detector plane and to a second position that is separated from the detector plane by a second distance in a direction perpendicular to the detector plane, the second distance being longer than the first distance,
      recognizes the specific region in which the subject is captured in respective frames constituting the dynamic image,
      generates an interpolation frame by determining an outline of the specific region for a source-to-image distance set to infinity, based on the specific region in a frame generated when the radiation source is in the first position and the specific region in a frame generated when the radiation source is in the second position, and
      replaces a frame of the dynamic image that is generated when the radiation source is at the second position with the interpolation frame.

4. The dynamic analysis system according to claim 1, further comprising:
   a storage that stores the dynamic image corrected by the position correction performed by the hardware processor.

5. The dynamic analysis system according to claim 1, further comprising:
   a display that displays the dynamic image corrected by the position correction performed by the hardware processor.

6. The dynamic analysis system according to claim 1, wherein
   the subject is a mark that is attached to a specific part or a vicinity of the specific part.

7. The dynamic analysis system according to claim 3, further comprising:
   an optical camera that monitors whether or not the subject is displaced in a direction perpendicular to the detector plane, wherein,
   when the optical camera detected that the subject is displaced in the direction perpendicular to the detector plane, the hardware processor moves the radiation source to the second position.

8. The dynamic analysis system according to claim 6, wherein
the specific part is a joint.

9. A non-transitory computer-readable storage medium storing a program causing a hardware processor of a correction apparatus that processes a dynamic image obtained by irradiation of a subject from a radiation irradiation apparatus and by dynamic imaging on dynamics of the subject detected by a detector, to:
recognize a specific region in which the subject is captured in each of the frames constituting the dynamic image,
measure a size of the specific region that has been recognized in the each of the frames, and
perform position correction on at least one frame of the dynamic image to ensure that a size of the specific region of the subject in the at least one frame and a size of the specific region of the subject in a reference frame of the dynamic image are within a predetermined range, thereby eliminating an effect of displacement of the subject in a direction perpendicular to a detector plane.

10. A dynamic analysis system that processes a dynamic image obtained by irradiation of a subject from a radiation irradiation apparatus and by dynamic imaging on dynamics of the subject detected by a detector, comprising:
a hardware processor that performs position correction of the dynamic image by eliminating an effect of displacement of the subject in a direction perpendicular to a detector plane,
wherein the radiation irradiation apparatus has a radiation source that moves in a direction perpendicular to the detector plane, and
wherein the hardware processor
moves the radiation source, while the subject is imaged, to a first position that is separated from the detector plane by a first distance in a direction perpendicular to the detector plane and to a second position that is separated from the detector plane by a second distance in a direction perpendicular to the detector plane, the second distance being longer than the first distance,
recognizes a specific region in which the subject is captured in respective frames constituting the dynamic image,
generates an interpolation frame by determining an outline of the specific region for a source-to-image distance set to infinity, based on the specific region in a frame generated when the radiation source is in the first position and the specific region in a frame generated when the radiation source is in the second position, and
replaces a frame of the dynamic image that is generated when the radiation source is at the second position with the interpolation frame.

11. The dynamic analysis system according to claim 10, further comprising:
an optical camera that monitors whether or not the subject is displaced in a direction perpendicular to the detector plane, wherein,
when the optical camera detected that the subject is displaced in the direction perpendicular to the detector plane, the hardware processor moves the radiation source to the second position.

* * * * *